United States Patent
Iarocci et al.

(10) Patent No.: US 7,299,641 B2
(45) Date of Patent: *Nov. 27, 2007

(54) CRYOGENIC STORAGE SYSTEM WITH IMPROVED TEMPERATURE CONTROL

(75) Inventors: Michael Iarocci, Patchogue, NY (US);
Stephen Valentine, New York, NY (US); Brian Wowk, Corona, CA (US)

(73) Assignee: The Stasis Foundation, Fort Lauderdale, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/299,578

(22) Filed: Dec. 12, 2005

(65) Prior Publication Data

US 2006/0090479 A1    May 4, 2006

Related U.S. Application Data (63) Continuation of application No. 10/867,987, filed on Jun. 14, 2004, now Pat. No. 6,988,370.

(60) Provisional application No. 60/477,863, filed on Jun. 12, 2003.

(51) Int. Cl.
*F17C 3/08* (2006.01)
*F17C 7/02* (2006.01)

(52) U.S. Cl. .......................... 62/45.1; 62/50.1

(58) Field of Classification Search ................ 62/45.1, 62/49.1, 50.1, 54.1
See application file for complete search history.

(56) References Cited

U.S. PATENT DOCUMENTS

| | | | | |
|---|---|---|---|---|
| 3,930,375 A | * | 1/1976 | Hofmann | 62/45.1 |
| 4,608,831 A | * | 9/1986 | Gustafson | 62/48.1 |
| 5,005,362 A | * | 4/1991 | Weltmer et al. | 62/45.1 |
| 5,065,582 A | * | 11/1991 | Seifert | 62/45.1 |
| 5,235,818 A | * | 8/1993 | Horikawa et al. | 62/51.1 |
| 5,243,821 A | * | 9/1993 | Schuck et al. | 62/50.6 |
| 5,357,758 A | * | 10/1994 | Andonian | 62/45.1 |
| 5,408,832 A | | 4/1995 | Boffito et al. | |
| 5,590,535 A | * | 1/1997 | Rhoades | 62/50.2 |
| 5,726,908 A | * | 3/1998 | Hosmer et al. | 702/55 |
| 5,787,940 A | * | 8/1998 | Bonn et al. | 141/18 |
| 5,960,633 A | * | 10/1999 | Limbach | 62/45.1 |

(Continued)

FOREIGN PATENT DOCUMENTS

| | | |
|---|---|---|
| EP | 0798523 A2 | 10/1997 |
| JP | 59-217296 A * | 12/1994 |

*Primary Examiner*—Mohammad M. Ali
(74) *Attorney, Agent, or Firm*—Carter, DeLuca, Farrell & Schmidt, LLP (57) ABSTRACT

A cryogenic storage system for cryogenic storage using liquid refrigerant is provided. The cryogenic storage system includes first and second vacuum vessels, a vacuum source, a quantity of a liquid refrigerant, and at least one temperature control assembly. An insulating wall may be provided on an interior surface of one of the vessels. A common vacuum condition is provided in voids that are present in the wall of the first and second vessels as well as in the insulating wall. The at least one temperature control assembly includes a power supply, a temperature sensor, a heater, and a conductive element. The at least one conductive element provides a link or thermal coupling between a space defined in the first vessel and the liquid refrigerant stored in the second vessel.

9 Claims, 7 Drawing Sheets

U.S. PATENT DOCUMENTS

| | | |
|---|---|---|
| 6,119,465 A | 9/2000 | Mullens et al. |
| 6,276,143 B1 * | 8/2001 | Wimberley ................. 62/50.2 |
| 6,505,469 B1 | 1/2003 | Drube et al. |
| 6,542,848 B1 | 4/2003 | Neeser et al. |
| 6,563,312 B2 | 5/2003 | Saho et al. |
| 6,609,383 B1 | 8/2003 | Kusada et al. |
| 6,631,615 B2 * | 10/2003 | Drube et al. ................. 62/50.4 |
| 6,655,156 B1 | 12/2003 | Miksic et al. |
| 6,668,561 B1 | 12/2003 | Sheu et al. |
| 6,672,077 B1 | 1/2004 | Bradley et al. |
| 6,708,502 B1 | 3/2004 | Aceves et al. |
| 6,782,339 B2 | 8/2004 | Neeser et al. |
| 6,810,924 B2 | 11/2004 | White |
| 6,898,985 B1 | 5/2005 | Gautreau |

\* cited by examiner

CRYOGENIC STORAGE SYSTEM WITH IMPROVED TEMPERATURE CONTROL

CROSS-REFERENCE TO RELATED APPLICATIONS

This application is a continuation of U.S. patent application Ser. No. 10/867,987, filed Jun. 14, 2004, now U.S. Pat. No. 6,988,370, which claimed priority from and the benefits of U.S. Provisional Application Ser. No. 60/477,863 filed on Jun. 12, 2003, the entire contents of each are hereby incorporated by reference in their entirety.

BACKGROUND

1. Technical Field

The present disclosure relates to cryogenic storage systems. More particularly, the present disclosure relates to a system for maintaining a variable but isothermal temperature in a cryogenic storage system.

2. Background of Related Art

Maintenance of material in a cryogenic storage system at low temperature is typically limited to specific temperature ranges associated with the properties of the particular cryogenic fluid used in the cryogenic storage system, e.g., about 77° K. for liquid nitrogen at a pressure of 1 atmosphere. If mechanical cryogenic refrigeration equipment is used, the properties of the selected refrigerant or cryogen govern the nominal operating temperature of the system, so selection of a particular temperature is again limited to the cryogens available having the temperature characteristics. Regardless of the refrigeration method selected, mechanical cryogenic refrigeration or bulk liquid cryogen, operation at a particular cryogenic temperature requires a different approach. Since both mechanical cryogenic refrigeration and bulk liquid cryogen refrigeration are limited in their temperature ranges, a need exists for maintaining a biological material in a cryogenic storage system.

A preferred refrigeration choice is the use of a saturated cryogen, in small quantities, which nominally produces stable and economical refrigeration for long periods in standard cryogenic Dewars.

An object of the present disclosure is to use a cryogen or refrigerant to maintain an isothermal volume at a stable temperature.

Another object of present disclosure is to allow the selection of a discrete temperature range for any given cryogen.

Yet another object of the present disclosure is to allow discrete temperature control within the selected temperature range.

SUMMARY

The present disclosure is directed towards a cryogenic storage system having improved temperature control. The cryogenic storage system includes first and second vessels or vacuum Dewars wherein the second vessel is configured for placement in the first vessel. First and second vessels have open ends adapted to sealingly mate with respective first and second lids. First and second spaces are defined by the respective open ends, respective closed ends, and respective first and second walls. The first and second vacuum Dewars includes respective first and second voids having a vacuum condition. The first and second voids may be fluidically coupled to form a common vacuum. A vacuum source may be provided for evacuating and maintaining the common vacuum in the first and second Dewars. Additionally, the vacuum source may be fluidly connected to a lateral insulating wall disposed upon an inner surface of the first vessel. A Mylar layer may be included on a bottom surface of the second lid and the first lid may be a vacuum insulated lid. A conductive liner may be included on an inner surface of the second vessel. The conductive liner may be formed from aluminum or another suitable thermally conductive material. A quantity of a liquid cryogen or refrigerant is stored in the first space of the first vessel. The liquid refrigerant may be liquid nitrogen. A fill tube is provided for adding the refrigerant to the first space. A support member is included for supporting the second vessel within the first vessel. An insulating panel may be disposed between the bottom of the second vessel and the support member. The insulating panel may be formed from evacuated aerogel material. At least one temperature control assembly may be provided. The at least one temperature control assembly may include a conductive element, a temperature sensor, a heater, a thermostatic controller, and a power supply.

In another embodiment of the present disclosure, a pipe may be included for connecting the first space to the second space. At least one temperature control assembly may be associated with the pipe. A plurality of legs is included for supporting the second vessel within the first vessel. Each leg may also be provided with a temperature control assembly.

BRIEF DESCRIPTION OF THE DRAWINGS

Embodiments of the present invention are described herein with reference to the accompanying drawings, wherein.

DETAILED DESCRIPTION OF PREFERRED EMBODIMENTS

Embodiments of the presently disclosed cryogenic storage system will now be described in detail with reference to the accompanying drawings, in which like reference numerals designate identical or corresponding elements in each of the several views.

Figure 1:
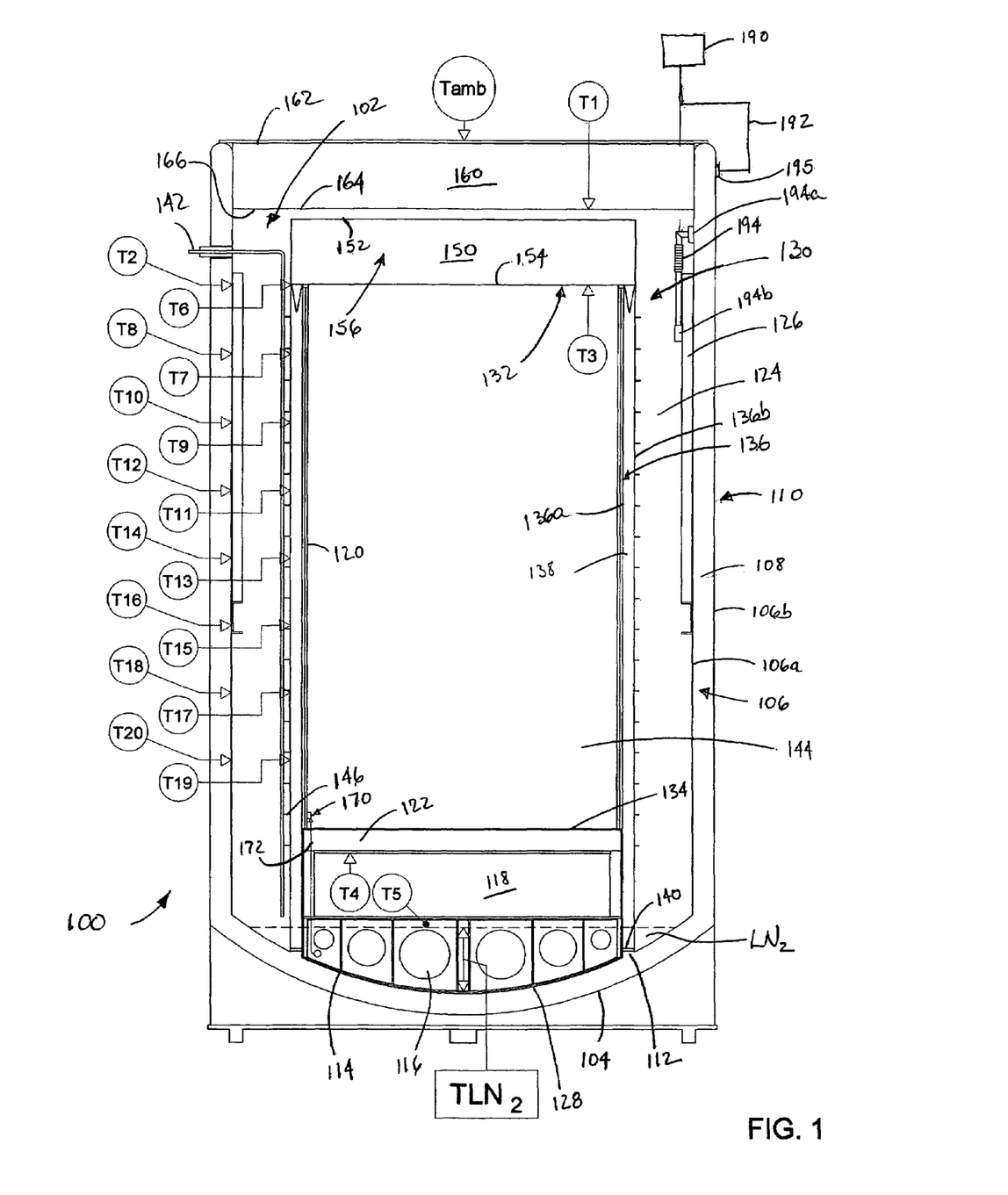
FIG. 1 is a side cross-sectional view of a first embodiment of the present invention showing a first vessel with a first lid and a second vessel with a second lid.

Referring initially to FIG. 1, a first embodiment of a temperature control system for a cryogenic storage volume in accordance with the present disclosure is shown and generally designated as 100. The cryogenic storage system 100 includes a first vessel or Dewar 110, a first lid 160, a second vessel or Dewar 130, a second lid 150, and a temperature control assembly 170. The first and second vessels 110, 130 have respective first and second open ends or tops 102, 132, respective first and second closed ends or bottoms 104, 134, and respective first and second walls 106, 136 which together define respective first and second spaces 124, 144. In one embodiment, the first and second vessels 110, 130 are vacuum Dewars as described more fully hereinbelow.

The first and second vessels 110, 130 are adapted for sealing engagement with their respective first and second lids 160, 150. Lids 150 and 160 are insulated structures adapted for releasable attachment to their respective first and second vessels 110, 130. The first lid 160 may be formed from foam or other suitable insulating materials as are known in the art. The first lid 160 has a top surface 162 and a bottom surface 164. The bottom surface 164 may include a reflective Mylar shield 166 for improving the insulating characteristics of the first lid 160. The second lid 150 is a vacuum insulated lid that has a top surface 152 and a bottom surface 154 defining a third void 156 therebetween that maintains the vacuum conditions for the second lid 150. As assembled and illustrated in FIG. 1, the first space 124 of the first vessel 110 is configured to receive the second vessel 130 and the second lid 150.

In one embodiment, the bottom 104 of the first vessel 110 is generally concave. At least one support member 114 is attached to the bottom 104 for supporting the second vessel 130 within the first vessel 110. A plurality of orifices 116 is disposed on the support member 114. A volume of a cryogen or liquid refrigerant is located in the first space or controlled volume 124 of the first vessel 110. In one embodiment, the cryogen is liquid nitrogen $LN_2$ although other known cryogens may be used. A fill tube 142 extends through a connection 146 on the first wall 106 for introducing the liquid nitrogen $LN_2$ into the first space 124. The fill tube 142 may be used to add additional liquid nitrogen $LN_2$ to the first space 124 as desired. A plurality of stiffening rings or spacers 146 is disposed along the outer surface 106b where they are vertically spaced apart for supporting the fill tube 142. The first space 124 is maintained at a pressure of about 1 atmosphere. Boiling of the liquid nitrogen $LN_2$ maintains the temperature of the first space 124 at the saturation temperature of liquid nitrogen $LN_2$ or about 77° K. therein. The temperature in the second space or controlled volume 144 may be varied within a range of about 80° K. to about 180° K. as discussed hereinbelow.

The orifices 116 allow the liquid nitrogen $LN_2$ to flow throughout the bottom of the first vessel 110 for maintaining a substantially even distribution of the liquid nitrogen $LN_2$ in the first vessel 110. In ascending order, an insulated panel 118 and a plate 122 are positioned between the support member 114 and the bottom 134 of the second vessel 130. In one embodiment, the insulated panel 118 is removable and may be formed from evacuated (i.e. vacuum) aerogel thereby increasing the thermal isolation between the second vessel 130 and the liquid nitrogen $LN_2$.

The first wall 106 of the first vessel 110 includes an inner surface 106a and an outer surface 106b that define a first gap or void 108 therebetween. In one embodiment, a lateral insulating wall 126 is disposed on the inner surface 106a for improving the insulating characteristics of the first wall 106. A quantity of gettering material 128, such as charcoal, may be disposed in the first void 108 where it is placed on the inner surface 106a along the concave portion which is opposite to the location where the liquid nitrogen $LN_2$ is located. The gettering material 128 provides cryopumping by cryoabsorption when the opposite surface is wetted with liquid nitrogen $LN_2$ that assists in maintaining the vacuum condition in the first void 108. Alternately, other known gettering materials may be used. Similarly, the second wall 136 of the second vessel 130 has an inner surface 136a and an outer surface 136b defining a second gap or void 138 therebetween. In one embodiment, each of the voids 108, 138 are under vacuum conditions, as described more fully hereinbelow, thereby defining first and second vessels or vacuum Dewars 110, 130. By having first and second vacuum Dewars 110, 130, a specific temperature may be maintained in the first vacuum Dewar 110 that is different from a temperature maintained in the second vacuum Dewar 130 since the vacuum conditions in the first and second voids 108, 138 provide thermal insulation for the first and second spaces 124, 144 respectively.

Each void 108, 138 is adapted to be connected to a vacuum source 190 through a vacuum line 192 to evacuate gases from the voids 108, 138 and maintain common vacuum conditions therein. In embodiments including the lateral insulating wall 126, common vacuum conditions are maintained in the voids 108, 138 and the lateral insulating wall. The vacuum line 192 fluidly connects each void 108, 138 to the vacuum source 190. In particular, a vacuum connection assembly 194 is attached to the inner surface 106a of the first vessel 110. The vacuum connection assembly 194 is an elongate tubular structure having first and second ports 194a and 194b disposed thereon. The first port 194a fluidly couples the vacuum connection assembly 194 to the first void 108 and the second port 194b fluidly couples the vacuum connection assembly 194 to the lateral insulating wall 126. A port 195 couples the vacuum line 192 to the first void 108 through outer surface 106b. The desired vacuum condition is maintained in the first void 108 by connecting the vacuum source 190 as described above.

Still referring to FIG. 1, the vacuum condition of the second void 138 is maintained as follows. The inner surface 106a of the first wall 106 includes at least one opening 112. The second wall 136 of the second vessel 130 has a corresponding number of openings 140 adapted to sealing mate with the at least one opening 112. In one embodiment, the inner surface 106a includes a plurality of openings 112 disposed in a substantially circumferential arrangement. By providing a plurality of complementary fluidly connected openings 112, 140, the vacuum condition is maintained in both voids 108, 138 without significantly reducing the structural strength and/or integrity of either vessel 110, 130.

The inner and outer surfaces 136a, 136b of the second wall 136 extend upwardly from the inner surface 106a of the first vessel 110. In one embodiment, a thermally conductive liner 120 is disposed along the inner surface 136a of the second vessel 130. The thermally conductive liner 120 may be formed from aluminum or other suitable thermally conductive materials (i.e. those having low thermal resistance) as are known in the art. The conductive liner 120 conducts heat in the second space 144. The conductive liner 120 has low thermal resistance and it conducts heat energy rapidly throughout the second space 144 thereby maintaining a substantially uniform temperature throughout the second space 144.

Figure 7:
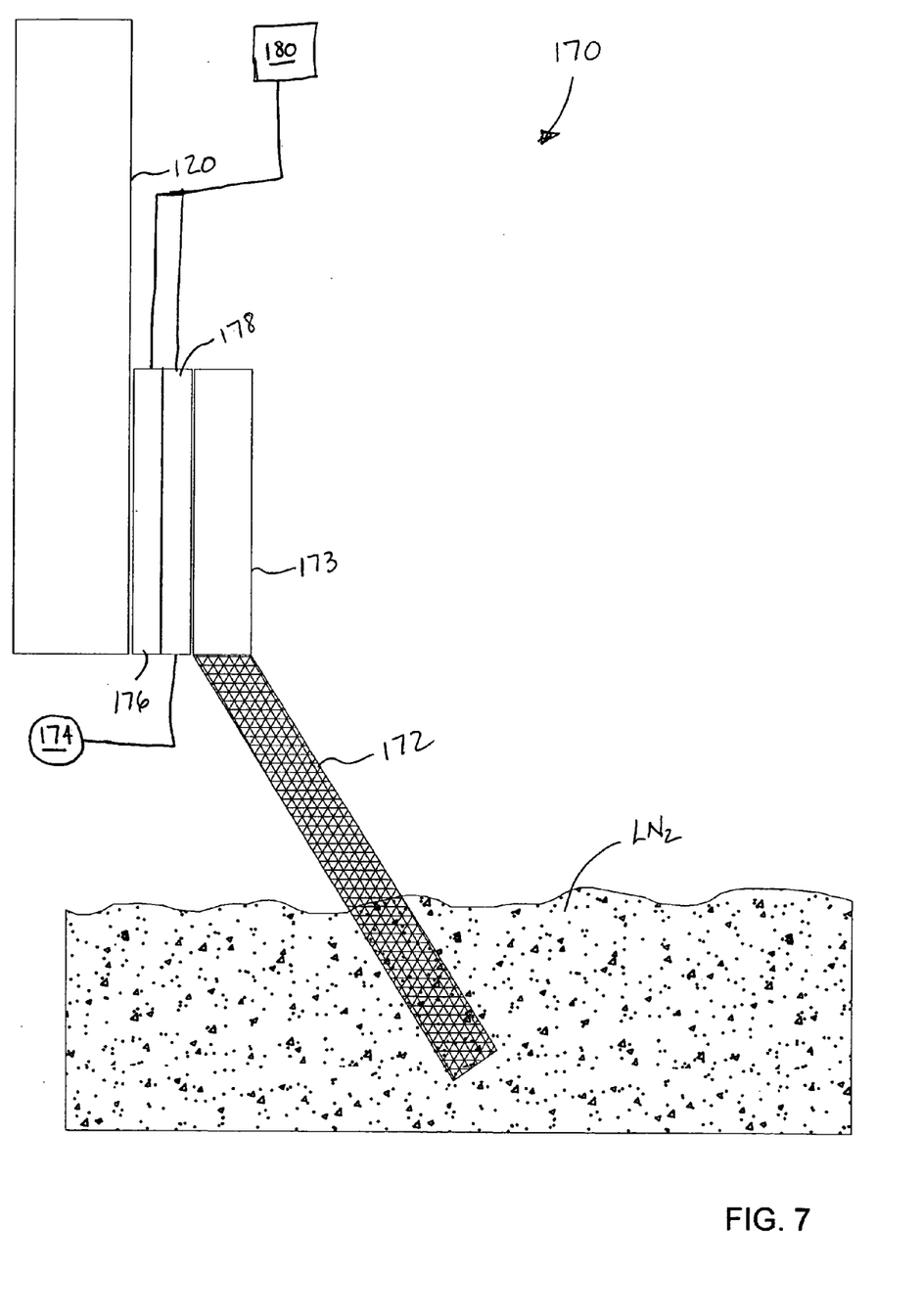
FIG. 7 is a side-cross sectional view of a temperature control assembly.

With reference to FIGS. 1 and 7, at least one temperature control assembly 170 is disposed near the bottom 134 of the second vessel 130 (see FIG. 1). The temperature control assembly 170 includes a conductive element or specific conductor 172, a temperature sensor 174, a heater 176, a thermostatic controller 178, and a power supply 180. One end of the conductive element 172 includes a connector 173 for attachment to the thermostatic controller 178. In one embodiment, the conductive element 172 is a metallic braid or rod formed from aluminum. In combination with the liquid nitrogen $LN_2$ or other cryogen, the material and/or dimensions of the conductive element 172 determines the operating temperature range of the cryogenic storage system 100. Alternately, other suitable thermally conductive materials may be used to link or thermally couple the second space 144 and the liquid nitrogen $LN_2$ stored in the first space 124 of the first vessel 110. The desired temperature range of operation is one of several factors that may determine the material used to form the conductive element 172. The conductive element 172 extends between the second space 144 and the liquid nitrogen $LN_2$ and may be adjustable to selectively extend into or be spaced from the liquid nitrogen $LN_2$.

The temperature of the second space 144 may be varied within a range of about 80° K to about 180° K as follows. As noted above, the temperature in the first space 124 is maintained at about 77° K (i.e. the saturation temperature of the liquid nitrogen $LN_2$). The second space 144 is thermally insulated from the first space 124 by the vacuum conditions in the second void 138 thereby allowing a different temperature from the first space 124 to be established and maintained therein. In one embodiment, the position of the conductive element 172 relative to the liquid nitrogen $LN_2$ is adjustable. The conductive element 172 may be spaced apart from the liquid nitrogen $LN_2$ or at least a portion of it may be immersed in the liquid nitrogen $LN_2$ as shown in FIG. 7. When at least partially immersed in the liquid nitrogen $LN_2$, heat energy is transferred from the second space 144 through the conductive element 172 to the liquid nitrogen $LN_2$ thereby reducing the temperature in the second space 144. Maintaining at least partial immersion of the conductive element 172 in the liquid nitrogen $LN_2$ will reduce the temperature of the second space 144 towards about 77° K. By reducing the amount of immersion or by spacing the conductive element 172 apart from the volume of liquid nitrogen $LN_2$, less heat energy is transferred from the second space 144 to the liquid nitrogen $LN_2$, thereby providing a temperature higher than about 77° K. Therefore, a temperature in the range of about 80° K to about 180° K may be maintained in the second space 144 even though the temperature in the first space 124 is maintained at saturation temperature (i.e. about 77° K). Additionally, the heater 176 is controlled by the thermostatic controller 178 for establishing and maintaining a desired temperature in cooperation with the conductive element 172 in the desired operating temperature range.

The thermostatic controller 178 alternately energizes and de-energizes the heater 176 for maintaining a desired temperature in the second space 144. In one embodiment, the desired temperature of the second space 144 is stored in the thermostatic controller 178 as a reference value. The thermostatic controller 178, as is known in the art, compares a temperature value from the temperature sensor 174 to the reference value stored therein. When the temperature value is greater than the reference value, the thermostatic controller 178 de-energizes the heater 176 to reduce the temperature in the second space 144 to the desired temperature value. Conversely, when the temperature value is less than the reference value, the thermostatic controller 178 energizes the heater 176 to raise the temperature in the second space 144 to the desired temperature value. Alternatively, the heater 176 and the thermostatic controller 178 may be combined into a single structure.

By combining the thermostatic controller 178 and the variable spacing of the conductive element 172, a temperature greater than about 77° K can be maintained in the second space 144. Using a selected heat balance design (i.e. the relative position of the conductive element 172 to the liquid nitrogen $LN_2$ and the combination of insulating structures), the target temperature in the second space 144 will be slightly lower than the desired temperature and a combination of the temperature sensor 174, the heater 176, and the thermostatic controller 178 will balance the second space 144 at the desired temperature within the operating temperature range of the cryogenic storage system 100.

Figure 2:
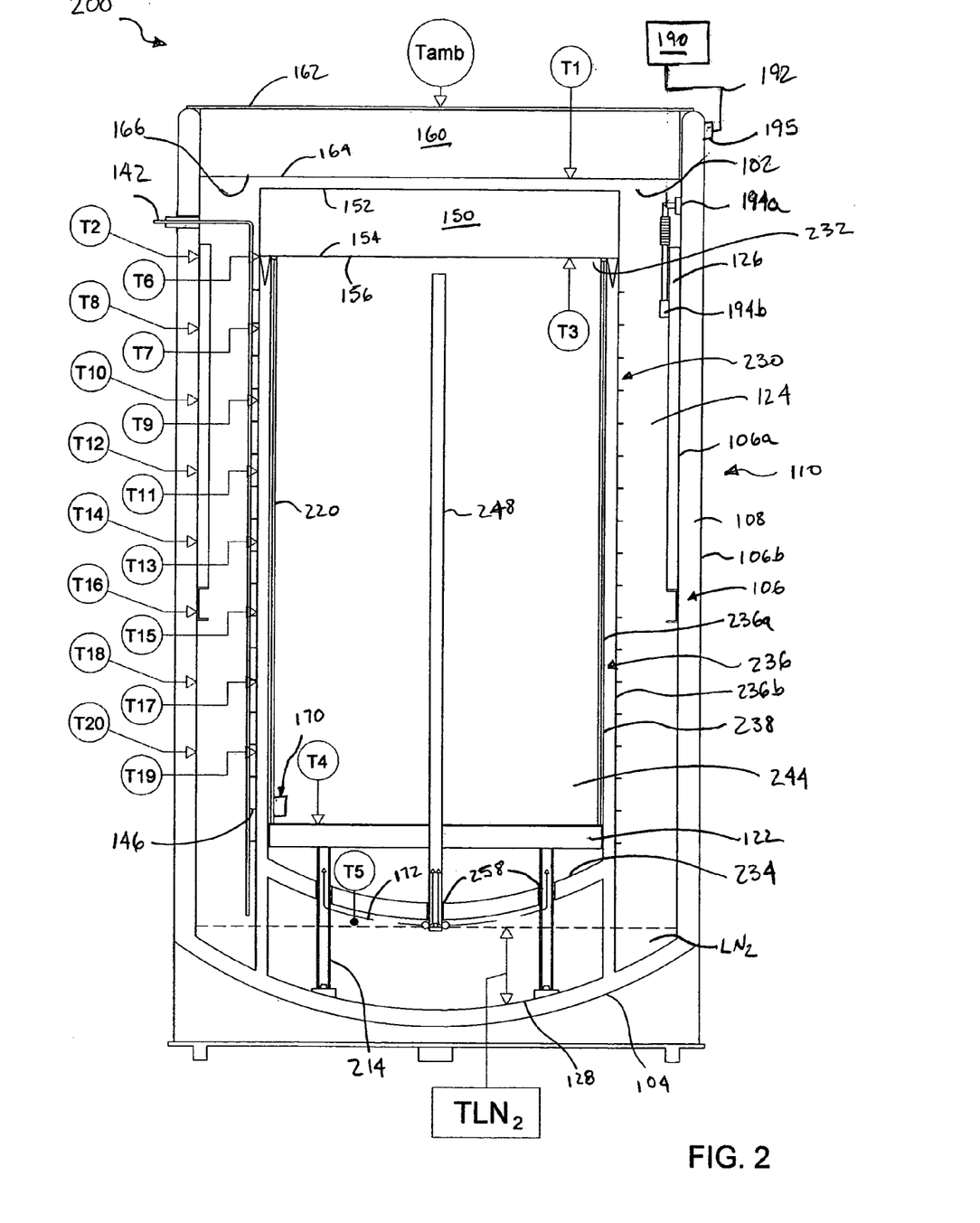
FIG. 2 is a side cross-sectional view of a second embodiment of the present invention showing a first vessel with a first lid and a second vessel with a second lid.

Referring now to FIGS. 2 and 7, a second embodiment of the cryogenic storage system 200 is illustrated. The cryogenic storage system 200 contains the same or substantially similar structures and identifiers as the cryogenic storage system 100 described above. Differences between the embodiments are described hereinbelow with reference to the alternate structures and their respective reference designations. The cryogenic storage system 200 includes a first vessel or Dewar 110, a second vessel or Dewar 230, a first lid 160, a second lid 150, and a temperature control assembly 170.

Second vessel 230 has a second open end or top 232, a second closed end or bottom 234, and a second wall 236. A second space 244 is defined in the second vessel 230 by the open end or top 232, the closed end or bottom 234, and the wall 236. The second wall 236 of the second vessel 230 has an inner surface 236a and an outer surface 236b defining a second gap or void 238 therebetween. In one embodiment, the second vessel 230 is a vacuum Dewar as described in detail in the previous embodiment. In one embodiment, a lateral insulating wall 126 is disposed on the inner surface 106a for improving the insulating characteristics of the first wall 106. The second vessel 230 is adapted to be received in the first space 124 of the first vessel 110 and is supported therein by a plurality of support members 214. Each of the support members 214 is a hollow elongate member that is adapted to receive the conductive element 172 therein to link or thermally couple the second space with the liquid nitrogen $LN_2$ stored in the first space 124. The support members extend substantially vertically from the inner surface 106a through the second wall 236 to support the plate 122. A space 218 is provided in lieu of the insulated panel 118 of the previous embodiment. In addition, the second vessel 230 includes an elongate hollow pipe 248 that extends through the plate 122. The pipe 248 is configured to receive the conductive element 172 of the temperature control assembly 170. The second wall 236 includes a plurality of throughholes 258 corresponding in number and location to the number and location of support members 214 and pipes 248.

In this embodiment, the second closed end 234 is a generally concave structure that is formed by the inner and outer surfaces 236a, 236b such that the second void 238 is common to the second wall 236 and the second closed end 234. Each of the throughholes 258 extends through the second wall 236 and does not provide a path between the second void 238 and either of the first space 144 or the second space 244. Further still, the second wall 236 has an open end that sealingly mates with the inner surface 106a of the first bottom 134 for fluidly connecting the first and second voids 108, 238. As in the previous embodiment, the first void 108 and the second void 238 are under a common vacuum condition from the vacuum source 190. In embodiments including the lateral insulating wall 126, the first and second voids 108, 238 have a common vacuum condition with the lateral insulating wall 126.

The at least one temperature control assembly 170 operates as previously discussed to control and/or maintain the selected temperature in the second space or control volume 244. By providing a temperature control assembly 170 in association with the pipe 248, additional temperature stability is provided in the second space 244.

Figure 3:
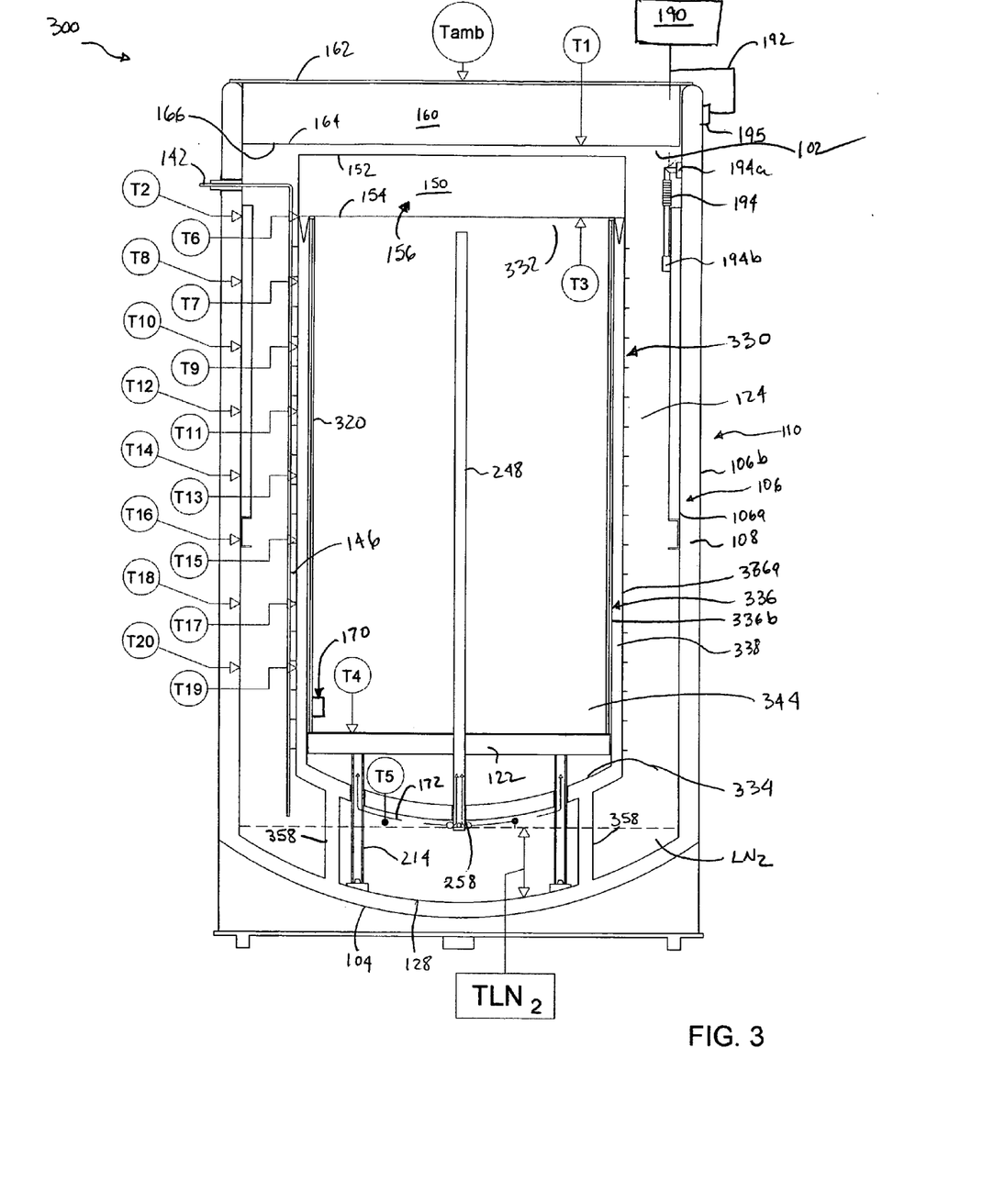
FIG. 3 is a side cross-sectional view of a third embodiment of the present invention showing a first vessel with a first lid and a second vessel with a second lid.

A third embodiment of the cryogenic storage system 300 is described with reference to FIGS. 3 and 7. The cryogenic storage system 300 contains the same or substantially similar structures and identifiers as the cryogenic storage systems 100 and 200 described hereinabove. Differences between the embodiments are described hereinbelow with reference to the alternate structures and their respective reference designations.

The cryogenic storage system 300 includes a first vessel or Dewar 110, a second vessel or Dewar 330, a first lid 160, a second lid 150, and a temperature control assembly 170. The second vessel 330 is similar to the second vessel 230 described hereinabove and includes a second wall 336, a second open end 332, and a second closed end 334. As in the previous embodiments, the inner and outer surfaces 336a, 336b define a second void 338. The second closed end 334 is generally concave and includes a pair of descending legs 358 for supporting the second vessel 330. In one embodiment, the legs 358 are hollow structures that fluidly connect the second void 338 with the first void 108 to provide a common vacuum condition for the voids 108, 338. Additionally, the legs 358 are spaced apart from the second wall 336 to provide additional vertical stability for the second vessel.

The at least one temperature control assembly 170 operates to maintain the desired temperature of the second space 344 as described in the previous embodiments.

Figure 4:
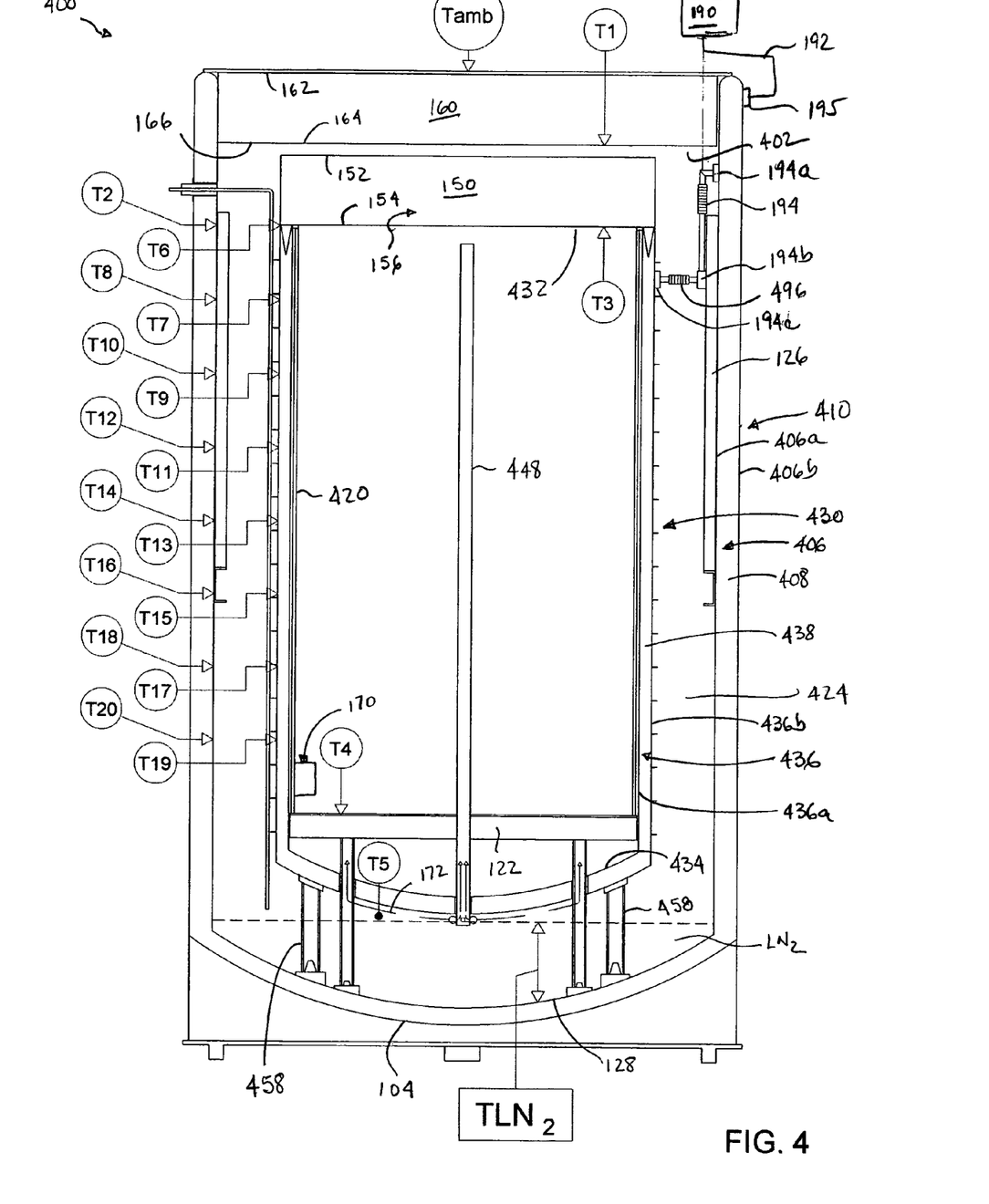
FIG. 4 is a side cross-sectional view of a fourth embodiment of the present invention showing a first vessel with a first lid and a second vessel with a second lid.

A fourth embodiment of the cryogenic storage system 400 is hereinafter described with reference to FIGS. 4 and 7. The cryogenic storage system 400 contains the same or substantially similar structures and identifiers as the cryogenic storage systems 100 and 200 described hereinabove. Differences between the embodiments are described hereinbelow with reference to the alternate structures and their respective reference designations.

The cryogenic storage system 400 includes a first vessel or Dewar 410, a first lid 160, a second vessel or Dewar 430, a second lid 150, and a temperature control assembly 170. The first and second vessels 410, 430 have respective first and second open ends or tops 402, 432, respective first and second closed ends or bottoms 404, 434, and respective first and second walls 406, 436. First and second spaces 424, 444 are defined in each vessel 410, 430 by the respective open ends 402, 432, respective closed ends 404, 434, and respective walls 406, 436. The first wall 406 of the first vessel 410 includes an inner surface 406a and an outer surface 406b that define a first gap or void 408 therebetween. In one embodiment, a lateral insulating wall 126 is disposed on the inner surface 406a for improving the insulating characteristics of the first wall 406. Similarly, the second wall 436 of the second vessel 430 has an inner surface 436a and an outer surface 436b defining a second gap or void 438 therebetween. In one embodiment, the first and second vessels 410, 430 are vacuum Dewars as described previously.

In particular, the first and second vessels 410, 430 are under a common vacuum condition as in the previous embodiments. In this embodiment, the connection between the first and second voids 408, 438 is through the vacuum connection assembly 194. In the previous embodiments, the vacuum connection assembly 194 included ports 194a and 194b for respectively connecting the first void 408 and the lateral insulating wall 126. The port 195 fluidly connects the vacuum line 192 to the first void 408 through the outer surface 406b. An additional port 194c is included on vacuum connection assembly 194 for fluidly connecting the vacuum source 190 to the second void 438. Specifically, the port 194d is coupled to a vacuum fitting 496 that is fluidly connected to the second void 438 whereby the first void 408, the second void 438, and the lateral insulating wall 126 are under a common vacuum condition as provided for by the vacuum source 190.

In addition, a plurality of legs 458 descend vertically from the outer surface 406b of the second vessel 430 and contact the inner surface 406b of the first vessel 410 to provide support for the second vessel 430. Each of the legs 458 do not fluidly connect the first void 408 with the second void 438 as in the previous embodiment, but are spatially arranged as before.

The at least one temperature control assembly 170 operates to maintain the desired temperature of the second space 444 as described in the previous embodiments.

Figure 5:
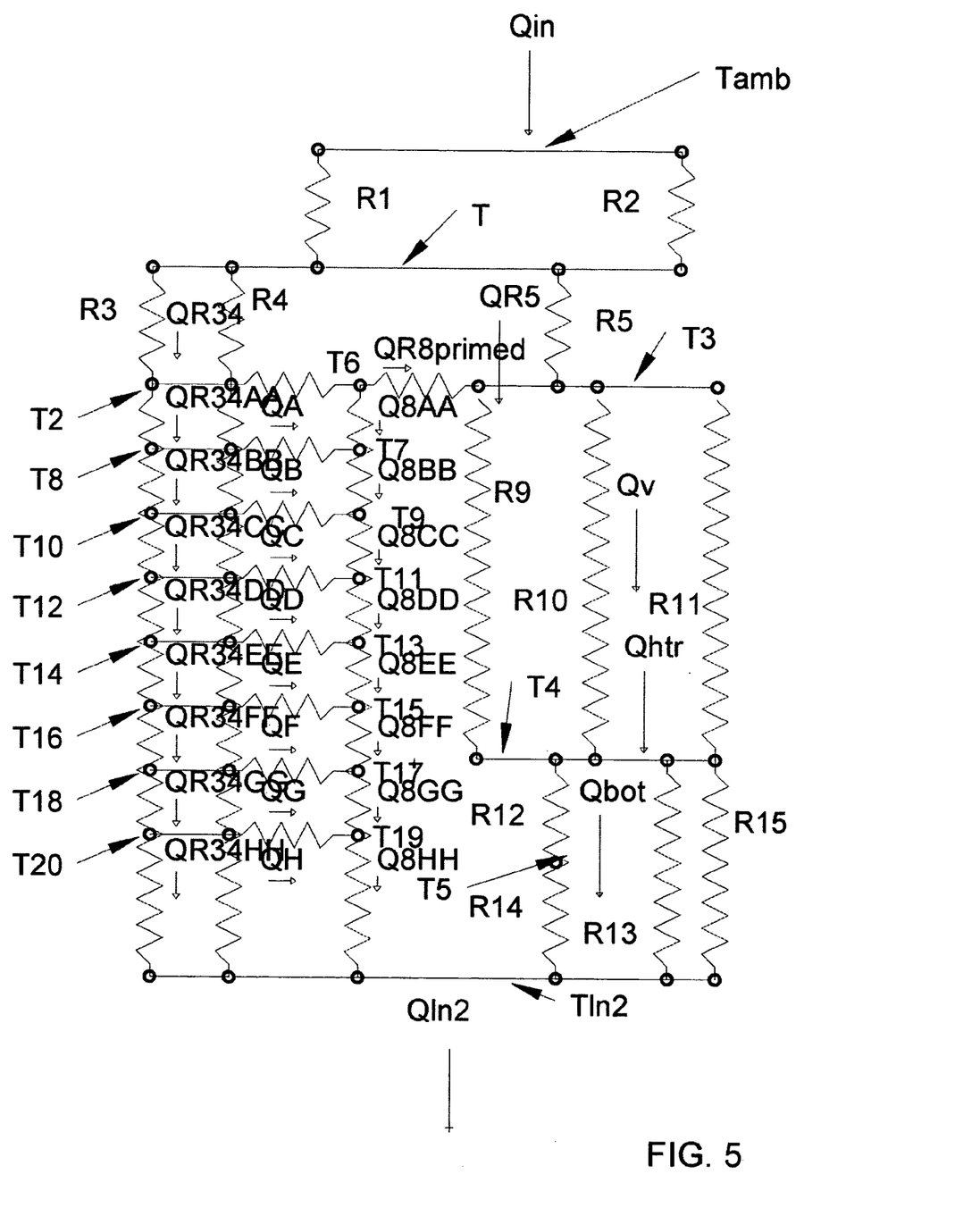
FIG. 5 is a schematic diagram illustrating an electrical analogy for analyzing the temperature and heat flow performance of the embodiment of FIG. 1.

An electrical analogy for analyzing the temperature and heat performance for the first embodiment is illustrated in FIG. 5. Referring additionally to FIG. 1, T1-T20 represent selected temperature analysis points, $T_{amb}$ represents the ambient temperature outside the cryogenic storage system 100, and $TLN_2$ represents the temperature of the liquid nitrogen $LN_2$. In addition, R1 is representative of the first lid 160, R2 and R3 represent the first wall 106, R4 represents nitrogen gas present in the first space 124 between the first lid 160 and the inner surface 106a, and R5 represents the second lid 150. QR34AA-QR34HH represents the heat flow down the inner surface 106a and the nitrogen gas in the first space 124. QA-QH represent the lateral conduction through the first and second voids 108, 138 while Q8AA-Q8HH is indicative of conduction down the outer surface 136b. Heat transferred to the second vessel 130 from the first space 144 is represented by QR8 primed. The outer surface 136b of the second wall 136 is represented by R8 while the inner surface 136a is represented by R9. R10 is indicative of the volume of nitrogen gas present in the first space 124 and R11 represents the conductive liner 120. R13 represents the conductive elements 172, R14 represents the nitrogen gas under the insulated panel 118, R12 represents the inner volume of the insulated panel 118, and the inner surface 136a that is proximal to the conductive elements 172 is represented by R15.

Figure 6:
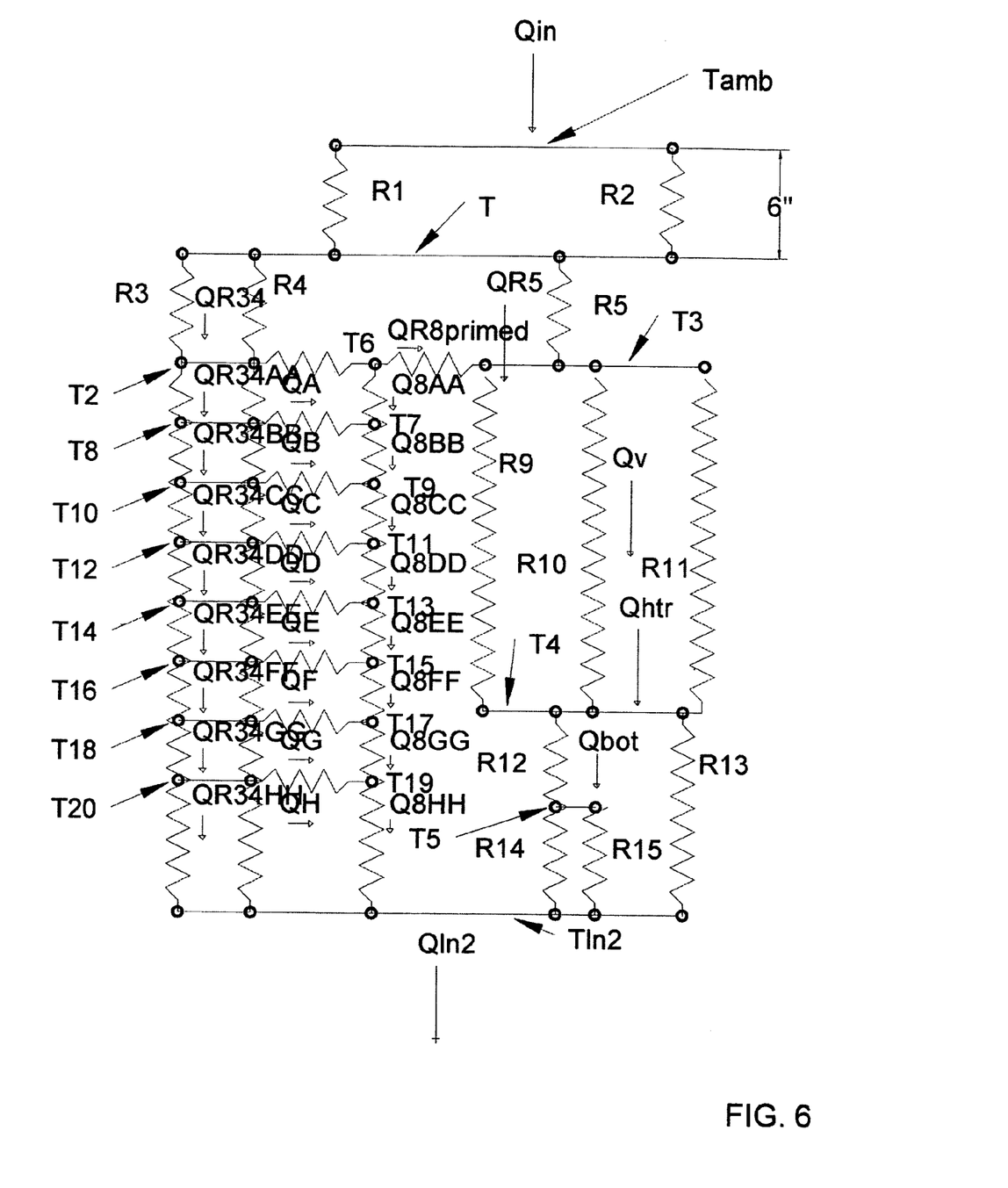
FIG. 6 is a schematic diagram illustrating an electrical analogy for analyzing the temperature and heat flow performance of the embodiments of FIGS. 2 and 3.

An electrical analogy for analyzing the temperature and heat performance for the second embodiment is illustrated in FIG. 6. Referring additionally to FIGS. 2-3, T1-T20 represent selected temperature analysis points, $T_{amb}$ represents the ambient temperature outside the cryogenic storage system 200, and $TLN_2$ represents the temperature of the liquid nitrogen $LN_2$. In addition, R1 is representative of the first lid 160, R2 and R3 represent the first wall 206, R4 represents nitrogen gas present in the first space 124 between the first lid 160 and the inner surface 106a, and R5 represents the second lid 150. QR34AA-QR34HH represents the heat flow down the inner surface 206a and the nitrogen gas in the first space 124. QA-QH represent the lateral conduction through the first and second voids 108, 238 while Q8AA-Q8HH is indicative of conduction down the outer surface 236b. Heat transferred to the second vessel 230 from the first space 124 is represented by QR8 primed. The outer surface 236b of the second wall 236 is represented by R8 while the inner surface 236a is represented by R9. R10 is indicative of the volume of nitrogen gas present in the first space 124 and R11 represents the conductive liner 120. R13 represents the conductive elements 172, R14 represents the nitrogen gas under the insulated panel 118, R12 represents the inner volume of the insulated panel 118, and the inner surface 236a that is proximal to the conductive elements 172 is represented by R15.

EXAMPLES

The performances of this invention are simulated by computer model. Performances for a few different configurations are given in the examples follow.

Example 1

Specific conductor equivalent diameter~0.5 cm and Controlled Volume Heater Power is 1 Watt.

Temperature Performance Data (Reference FIGS. 1 and 5): Version=1

| For power input> Qhtr = 1 W and conductive diameter> DC = 0.505 cm | | | |
|---|---|---|---|
| T_amb = 290K | T7 = 168.478K | T13 = 132.015K | T19 = 91.512K |
| T1 = 249.523K | T8 = 175.374K | T14 = 132.07K | T20 = 91.512K |
| T2 = 200.118K | T9 = 158.254K | T15 = 118.529K | T_LN2 = 78K |
| T3 = 133.431K | T10 = 159.627K | T16 = 118.54K | |
| T4 = 131.562K | T11 = 145.397K | T17 = 105.022K | |
| T6 = 165.468K | T12 = 145.67K | T18 = 105.025K | |

Note Controlled Volume Top and Bottom temperature figures T3 and T4

Liquid Nitrogen Consumption (without external Dewar sidewall and bottom heat load included):

Liquid nitrogen usage for: Version=1 nominal controlled temperature T3=133.431K and for power input>Qhtr=1 W and conductive diameter>DC=0.505 cm $$LN2\_consumption = 0.343 \frac{L}{hr}$$

Example 2

Specific conductor equivalent diameter~0.5 cm and Controlled Volume Heater Power is 2 Watts.

Temperature Performance Data (Reference FIGS. 1 and 5): Version=1

| For power input> Qhtr = 2 W and conductive diameter> DC = 0.505 cm | | | |
|---|---|---|---|
| T_amb = 290K | T7 = 171.474K | T13 = 133.616K | T19 = 91.911K |
| T1 = 250.777K | T8 = 175.374K | T14 = 133.668K | T20 = 91.912K |
| T2 = 202.646K | T9 = 160.693K | T15 = 119.729K | T_LN2 = 78K |
| T3 = 140.077K | T10 = 162K | T16 = 119.74K | |
| T4 = 138.33K | T11 = 147.404K | T17 = 105.822K | |
| T6 = 169.655K | T12 = 147.664K | T18 = 105.824K | |

Note Controlled Volume Top and Bottom temperature figures T3 and T4

Liquid Nitrogen Consumption (without external Dewar sidewall and bottom heat load included):

Liquid nitrogen usage for: Version=1 nominal controlled temperature T3=140.077K and for power input>Qhtr=2 W and conductive diameter>DC=0.505 cm $$LN2\_consumption = 0.356 \frac{L}{hr}$$

Example 3

Specific conductor equivalent diameter~0.5 cm and Controlled Volume Heater Power is 3 Watts.

Temperature Performance Data (Reference FIGS. 1 and 5): Version=1

| For power input> Qhtr = 3 W and conductive diameter> DC = 0.505 cm | | | |
|---|---|---|---|
| T_amb = 290K | T7 = 174.47K | T13 = 135.218K | T19 = 92.311K |
| T1 = 252.032K | T8 = 175.374K | T14 = 135.267K | T20 = 92.312K |
| T2 = 205.173K | T9 = 163.132K | T15 = 120.929K | T_LN2 = 78K |
| T3 = 146.724K | T10 = 164.373K | T16 = 120.939K | |
| T4 = 145.098K | T11 = 149.412K | T17 = 106.622K | |
| T6 = 173.842K | T12 = 149.659K | T18 = 106.624K | |

Note Controlled Volume Top and Bottom temperature figures T3 and T4

Liquid Nitrogen Consumption (without external Dewar sidewall and bottom heat load included):

Liquid nitrogen usage for: Version=1 nominal controlled temperature T3=146.724K and for power input>Qhtr=3 W and conductive diameter>DC=0.505 cm $$LN2\_consumption = 0.368 \frac{L}{hr}$$

Examples 4 to 6 reduce the conductive element equivalent diameter so to increase the Controlled Volume Temperature, thus achieving a higher temperature range.

Example 4

Specific conductor equivalent diameter~0.25 cm and Controlled Volume Heater Power is 1 Watt.

Temperature Performance Data (Reference FIGS. 1 and 5): Version=1

| For power input> Qhtr = 1 W and conductive diameter> DC = 0.252 cm | | | |
|---|---|---|---|
| T_amb = 290K | T7 = 169.465K | T13 = 132.543K | T19 = 91.643K |
| T1 = 249.936K | T8 = 175.374K | T14 = 132.596K | T20 = 91.644K |
| T2 = 200.951K | T9 = 159.058K | T15 = 118.925K | T_LN2 = 78K |
| T3 = 135.621K | T10 = 160.409K | T16 = 118.935K | |
| T4 = 133.792K | T11 = 146.058K | T17 = 105.286K | |
| T6 = 166.848K | T12 = 146.327K | T18 = 105.288K | |

Note Controlled Volume Top and Bottom temperature figures T3 and T4

Liquid Nitrogen Consumption (without external Dewar sidewall and bottom heat load included):

Liquid nitrogen usage for: Version=1 nominal controlled temperature T3=135.605K and for power input>Qhtr=1 W and conductive diameter>DC=0.255 cm $$LN2\_consumption = 0.34 \frac{L}{hr}$$

Example 5

Specific conductor equivalent diameter~0.25 cm and Controlled Volume Heater Power is 2 Watts.

Temperature Performance Data (Reference FIGS. 1 and 5): Version=1

| For power input> Qhtr = 2 W and conductive diameter> DC = 0.252 cm | | | |
|---|---|---|---|
| T_amb = 290K | T7 = 172.586K | T13 = 134.211K | T19 = 92.06K |
| T1 = 251.243K | T8 = 175.374K | T14 = 134.261K | T20 = 92.06K |
| T2 = 203.584K | T9 = 161.598K | T15 = 120.175K | T_LN2 = 78K |
| T3 = 142.544K | T10 = 162.88K | T16 = 120.185K | |
| T4 = 140.842K | T11 = 148.149K | T17 = 106.119K | |
| T6 = 171.209K | T12 = 148.404K | T18 = 106.121K | |

Note Controlled Volume Top and Bottom temperature figures T3 and T4

Liquid Nitrogen Consumption (without external Dewar sidewall and bottom heat load included):

Liquid nitrogen usage for: Version=1 nominal controlled temperature T3=142.527K and for power input>Qhtr=2 W and conductive diameter>DC=0.255 cm $$LN2\_consumption = 0.352 \frac{L}{hr}$$

Example 6

Specific conductor equivalent diameter~0.25 cm and Controlled Volume Heater Power is 5 Watts.

Temperature Performance Data (Reference FIGS. 1 and 5): Version=1

| For power input> Qhtr = 5 W and conductive diameter> DC = 0.252 cm | | | |
|---|---|---|---|
| T_amb = 290K | T7 = 181.948K | T13 = 139.214K | T19 = 93.31K |
| T1 = 255.162K | T8 = 175.374K | T14 = 139.257K | T20 = 93.31K |
| T2 = 211.483K | T9 = 169.218K | T15 = 123.925K | T_LN2 = 78K |
| T3 = 163.314K | T10 = 170.295K | T16 = 123.933K | |
| T4 = 161.99K | T11 = 154.422K | T17 = 108.619K | |
| T6 = 184.294K | T12 = 154.636K | T18 = 108.621K | |

Note Controlled Volume Top and Bottom temperature figures T3 and T4

Liquid Nitrogen Consumption (without external Dewar sidewall and bottom heat load included):

Liquid nitrogen usage for: Version=1 nominal controlled temperature T3=163.291K and for power input>Qhtr=5 W and conductive diameter>DC=0.255 cm $$LN2\_consumption = 0.388 \frac{L}{hr}$$

Examples 7 and 8 increase the conductive element equivalent diameter so to decrease the Controlled Volume Temperature, thus achieving a lower temperature range.

Example 7

Specific conductor equivalent diameter~1.5 cm and Controlled Volume Heater Power is 1 Watt.

Temperature Performance Data (Reference FIGS. 1 and 5): Version=1

| For power input> Qhtr = 1 W and conductive diameter> DC = 1.514 cm | | | |
|---|---|---|---|
| T_amb = 290K | T7 = 161.391K | T13 = 128.228K | T19 = 90.565K |
| T1 = 246.556K | T8 = 175.374K | T14 = 128.288K | T20 = 90.566K |
| T2 = 194.138K | T9 = 152.486K | T15 = 115.69K | T_LN2 = 78K |
| T3 = 117.708K | T10 = 154.014K | T16 = 115.703K | |
| T4 = 115.553K | T11 = 140.648K | T17 = 103.13K | |
| T6 = 155.563K | T12 = 140.952K | T18 = 103.133K | |

Note Controlled Volume Top and Bottom temperature figures T3 and T4

Liquid Nitrogen Consumption (without external Dewar sidewall and bottom heat load included):

Liquid nitrogen usage for: Version=1 nominal controlled temperature T3=117.701K and for power input>Qhtr=1 W and conductive diameter>DC=1.514 cm $$LN2\_consumption = 0.367 \frac{L}{hr}$$

Example 8

Specific conductor equivalent diameter~1.5 cm and Controlled Volume Heater Power is 3 Watts.

Temperature Performance Data (Reference FIGS. 1 and 5): Version=1

| For power input> Qhtr = 3 W and conductive diameter> DC = 1.514 cm | | | |
|---|---|---|---|
| T_amb = 290K | T7 = 165.592K | T13 = 130.473K | T19 = 91.126K |
| T1 = 248.315K | T8 = 175.374K | T14 = 130.53K | T20 = 91.127K |
| T2 = 197.683K | T9 = 155.905K | T15 = 117.373K | T_LN2 = 78K |
| T3 = 127.028K | T10 = 157.341K | T16 = 117.385K | |
| T4 = 125.043K | T11 = 143.463K | T17 = 104.252K | |
| T6 = 161.435K | T12 = 143.749K | T18 = 104.254K | |

Note Controlled Volume Top and Bottom temperature figures T3 and T4

Liquid Nitrogen Consumption (without external Dewar sidewall and bottom heat load included):

Liquid nitrogen usage for: Version=1 nominal controlled temperature T3=127.019K and for power input>Qhtr=3 W and conductive diameter>DC=1.514 cm $$LN2\_consumption = 0.398 \frac{L}{hr}$$

Example 9

Specific conductor equivalent diameter~3.3 cm and Controlled Volume Heater Power is 1 Watt.

Temperature Performance Data (Reference FIGS. 2 and 6): Version=2

| For power input> Qhtr = 1 W and conductive diameter> DC = 3.328 cm | | | |
|---|---|---|---|
| T_amb = 290K | T7 = 152.279K | T13 = 123.358K | T19 = 89.349K |
| T1 = 243.808K | T8 = 172.682K | T14 = 123.426K | T20 = 89.35K |
| T2 = 186.451K | T9 = 145.069K | T15 = 112.041K | T_LN2 = 78K |
| T3 = 97.494K | T10 = 146.797K | T16 = 112.054K | |
| T4 = 94.97K | T11 = 134.543K | T17 = 100.698K | |
| T6 = 142.829K | T12 = 134.887K | T18 = 100.7K | |

Note Controlled Volume Top and Bottom temperature figures T3 and T4

Liquid Nitrogen Consumption (without external Dewar sidewall and bottom heat load included):

Liquid nitrogen usage for: Version=2 nominal controlled temperature T3=97.494K and for power input>Qhtr=1 W and conductive diameter>DC=3.328 cm $$LN2\_consumption = 0.397 \frac{L}{hr}$$

It will be understood that various modifications may be made to the embodiments disclosed herein. Therefore, the above description should not be construed as limiting, but merely as an exemplification of preferred embodiments. Those skilled in the art will envision other modifications within the scope and spirit of the claims appended hereto.

What is claimed is:

1. A system for maintaining temperature in a space comprising:
   a first vessel having a closed end and an open end defining a first space;
   a second vessel having a closed end and an open end defining a second space, the first space configured for receiving the second vessel through the open end of the first vessel;
   a volume of a liquid refrigerant disposed in the first vessel; and
   at least one temperature control assembly operably associated with the system, the at least one temperature control assembly including a temperature sensor for sensing the temperature within the first or second spaces, a heater, and a thermostatic controller.

2. The system of claim 1, wherein the at least one temperature control assembly further comprises a conductive element that operably couples the temperature sensor and the liquid refrigerant.

3. The system of claim 2, wherein at least a portion of the conductive element is repositionable between a first position that is in contact with the liquid refrigerant and a second position that is spaced from the liquid refrigerant.

4. The system of claim 1, further including a liner formed from a thermally conductive material disposed on an inner surface of the second vessel.

5. The system of claim 1, further comprising first and second insulating covers adapted for releasably engaging the open ends of the respective first and second vessels.

6. The system of claim 1, wherein the first vessel includes a first wall having a void therein, the second vessel includes a second wall having a second void therein and a vacuum system including a vacuum source, said vacuum system in fluid communication with said first and second voids for creating a vacuum therein.

7. The system of claim 1, wherein the second vessel further includes an inner conductive wall.

8. The system of claim 7, wherein the at least one temperature control assembly is attached to the inner conductive wall.

9. The system of claim 8, wherein the at least one temperature control assembly further comprises a conductive element that operably couples the temperature sensor, the inner conductive wall, and the liquid refrigerant.

* * * * *